(12) United States Patent
Shubinsky et al.

(10) Patent No.: US 11,298,456 B2
(45) Date of Patent: Apr. 12, 2022

(54) INFUSION SYSTEM AND METHOD WHICH UTILIZES DUAL WAVELENGTH OPTICAL AIR-IN-LINE DETECTION

(71) Applicant: ICU Medical, Inc., San Clemente, CA (US)

(72) Inventors: Gary David Shubinsky, Buffalo Grove, IL (US); Tamas Ban, Grayslake, IL (US); Brian G. Markey, Park Forest, IL (US)

(73) Assignee: ICU Medical, Inc., San Clemente, CA (US)

( * ) Notice: Subject to any disclaimer, the term of this patent is extended or adjusted under 35 U.S.C. 154(b) by 153 days.

(21) Appl. No.: 16/505,479

(22) Filed: Jul. 8, 2019

(65) Prior Publication Data

US 2020/0069864 A1 Mar. 5, 2020

Related U.S. Application Data

(63) Continuation of application No. 14/633,614, filed on Feb. 27, 2015, now Pat. No. 10,342,917.

(Continued)

(51) Int. Cl.
*A61M 5/14* (2006.01)
*A61M 5/168* (2006.01)
(Continued)

(52) U.S. Cl.
CPC .......... *A61M 5/14* (2013.01); *A61M 5/16831* (2013.01); *A61M 5/365* (2013.01);
(Continued)

(58) Field of Classification Search
CPC .... A61M 5/14; A61M 5/16831; A61M 5/365; A61M 5/172; A61M 2205/3313; A61M 2205/50
See application file for complete search history.

(56) References Cited

U.S. PATENT DOCUMENTS 4,857,050 A * 8/1989 Lentz .................. G01F 23/2921
604/67
5,304,216 A 4/1994 Wallace
(Continued)

FOREIGN PATENT DOCUMENTS

AU 2013216679 9/2013
JP 07-502678 3/1995
(Continued)

OTHER PUBLICATIONS

"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. http://archive.epo.org/epo/pubs/oj013/11_13/11_5033.pdf.

(Continued)

*Primary Examiner* — Bradley J Osinski
(74) *Attorney, Agent, or Firm* — Knobbe Martens Olson & Bear, LLP (57) ABSTRACT

Infusion fluid is flowed through a fluid delivery line of an infusion system. Optical signals having different wavelengths are transmitted through the fluid delivery line. The transmitted optical signals having the different wavelengths are received. At least one processor determines whether air or infusion fluid is disposed in the fluid delivery line based on the received optical signals having the different wavelengths.

17 Claims, 10 Drawing Sheets

Related U.S. Application Data (60) Provisional application No. 61/946,031, filed on Feb. 28, 2014.

(51) Int. Cl.
*A61M 5/36* (2006.01)
*A61M 5/172* (2006.01)

(52) U.S. Cl.
CPC ..... *A61M 5/172* (2013.01); *A61M 2205/3313* (2013.01); *A61M 2205/50* (2013.01)

(56) References Cited

U.S. PATENT DOCUMENTS

| | | | |
|---|---|---|---|
| 5,734,464 | A * | 3/1998 | Gibbs ............... A61M 1/367 356/39 |
| 7,347,854 | B2 | 3/2008 | Shelton et al. |
| 8,002,736 | B2 | 8/2011 | Patrick et al. |
| 8,221,395 | B2 | 7/2012 | Shelton et al. |
| 8,523,797 | B2 | 9/2013 | Lowery et al. |
| 9,764,087 | B2 | 9/2017 | Peterfreund et al. |
| 9,852,265 | B1 | 12/2017 | Treacy et al. |
| 9,995,611 | B2 | 6/2018 | Ruchti et al. |
| 10,022,498 | B2 | 7/2018 | Ruchti et al. |
| 10,046,112 | B2 | 8/2018 | Oruklu et al. |
| 10,089,055 | B1 | 10/2018 | Fryman |
| 10,166,328 | B2 | 1/2019 | Oruklu et al. |
| 10,342,917 | B2 | 7/2019 | Shubinsky et al. |
| 10,430,761 | B2 | 10/2019 | Hume et al. |
| 2003/0186833 | A1 | 10/2003 | Huff et al. |
| 2003/0216682 | A1 | 11/2003 | Junker |
| 2006/0079768 | A1 | 4/2006 | Small et al. |
| 2006/0224140 | A1 | 10/2006 | Junker |
| 2007/0083152 | A1 | 4/2007 | Williams, Jr. et al. |
| 2007/0088271 | A1 | 4/2007 | Richards |
| 2007/0093753 | A1 | 4/2007 | Krulevitcvh et al. |
| 2010/0114027 | A1 | 5/2010 | Jacobson et al. |
| 2010/0168535 | A1 | 7/2010 | Robinson et al. |
| 2010/0185182 | A1 | 7/2010 | Alme et al. |
| 2010/0271218 | A1 | 10/2010 | Hoag et al. |
| 2011/0071844 | A1 | 3/2011 | Cannon et al. |
| 2011/0106561 | A1 | 5/2011 | Eaton, Jr. et al. |
| 2013/0012880 | A1 | 1/2013 | Blomquist |
| 2013/0197930 | A1 | 8/2013 | Garibaldi et al. |
| 2013/0274576 | A1 | 10/2013 | Amirouche et al. |
| 2013/0281965 | A1 | 10/2013 | Kamen et al. |
| 2015/0168958 | A1 | 6/2015 | Downie et al. |
| 2015/0224252 | A1 | 8/2015 | Borges et al. |
| 2015/0338340 | A1* | 11/2015 | Jiang ............... A61B 5/082 600/532 |
| 2016/0339167 | A1 | 11/2016 | Ledford et al. |
| 2018/0018440 | A1 | 1/2018 | Sugawara |
| 2019/0091401 | A1 | 3/2019 | Ruchti et al. |
| 2019/0101425 | A1 | 4/2019 | Ruchti et al. |
| 2019/0117890 | A1 | 4/2019 | Oruklu et al. |
| 2019/0196770 | A1 | 6/2019 | Fryman |
| 2019/0262535 | A1 | 8/2019 | Shubinsky et al. |
| 2019/0282757 | A1 | 9/2019 | Gylland et al. |

FOREIGN PATENT DOCUMENTS

| | | |
|---|---|---|
| JP | 2000-515716 | 11/2000 |
| JP | 2002-506514 | 2/2002 |
| JP | 2007-520270 | 7/2007 |
| JP | 2010-063767 | 3/2010 |
| WO | WO 96/028209 | 9/1996 |
| WO | WO 2004/070556 | 8/2004 |
| WO | WO 2008/019016 | 2/2008 |
| WO | WO 2012/082599 | 6/2012 |
| WO | WO 2012/167090 | 12/2012 |

OTHER PUBLICATIONS

"Decision of the Administrative Council of Oct. 27, 2009 Amending the Implementing Regulations to the European Patent Convention (CA/D 20/09)", Official Journal EPO Dec. 2009, Dec. 2009, pp. 582-584. http://archive.epo.org/epo/pubs/oj009/12_09/12_5829.pdf.

Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.

* cited by examiner

INFUSION SYSTEM AND METHOD WHICH UTILIZES DUAL WAVELENGTH OPTICAL AIR-IN-LINE DETECTION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Disclosure

This disclosure relates to an infusion system and method, which transmits and receives optical signals having different wavelengths to detect whether air is disposed in the infusion system.

Background

Different types of infusion systems exist for detecting whether air is present in the infusion fluid. Some infusion systems currently use one or more ultrasound sensors to determine whether air is present in the fluid disposed by the infusion system. However, some of these sensors are sensitive to debris such as dirt or residue from the cleaning solution being disposed in the sensor location on the fluid delivery line, which may lead to inaccurate results. Similarly, some of these sensors are sensitive to mechanical alignment or positioning, which affects their accuracy and long term stability.

A system and method is needed to overcome one or more issues of one or more of the current infusion systems and methods in order to detect whether air is in the fluid disposed by the infusion system.

SUMMARY

In one embodiment, an infusion system is disclosed for being operatively connected to a fluid delivery line connected to a container containing an infusion fluid. The infusion system includes at least two optical transmitters, at least one optical receiver, at least one processor, and a memory. The at least two optical transmitters are configured to transmit optical signals having different wavelengths through the fluid delivery line. The at least one optical receiver is configured to receive the optical signals having the different wavelengths transmitted from the at least two optical transmitters. The at least one processor is in electronic communication with the at least two optical transmitters and the at least one optical receiver. The memory is in electronic communication with the at least one processor. The memory contains programming code for execution by the at least one processor. The programming code is configured to determine whether air or the infusion fluid is disposed in the fluid delivery line based on the received optical signals having the different wavelengths which are received by the at least one optical receiver.

In another embodiment, a method for infusing an infusion fluid is disclosed. In one step, the infusion fluid is flowed through a fluid delivery line of an infusion system. In another step, optical signals having different wavelengths are transmitted through the fluid delivery line. In still another step, the transmitted optical signals having the different wavelengths are received. In yet another step, at least one processor determines whether air or infusion fluid is disposed in the fluid delivery line based on the received optical signals having the different wavelengths.

In an additional embodiment, an infusion system is disclosed for being operatively connected to a fluid delivery line connected to a container containing an infusion fluid. The infusion system includes one optical transmitter, at least one optical beam splitter, at least two optical beam filters, at least two optical receivers, at least one processor, and a memory. The one optical transmitter is configured to transmit a broad spectrum optical signal. The at least one optical beam splitter is configured to split the broad spectrum optical signal into two separate beams. The at least two optical filters are configured to filter the two separate beams. The at least two optical receivers are configured to receive the filtered two separate beams. The at least one processor is in electronic communication with the one optical transmitter and the at least two optical receivers. The memory is in electronic communication with the at least one processor. The memory contains programming code for execution by the at least one processor. The programming code is configured to determine whether air or the infusion fluid is disposed in the fluid delivery line based on the received filtered two separate beams which are received by the at least two optical receivers.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
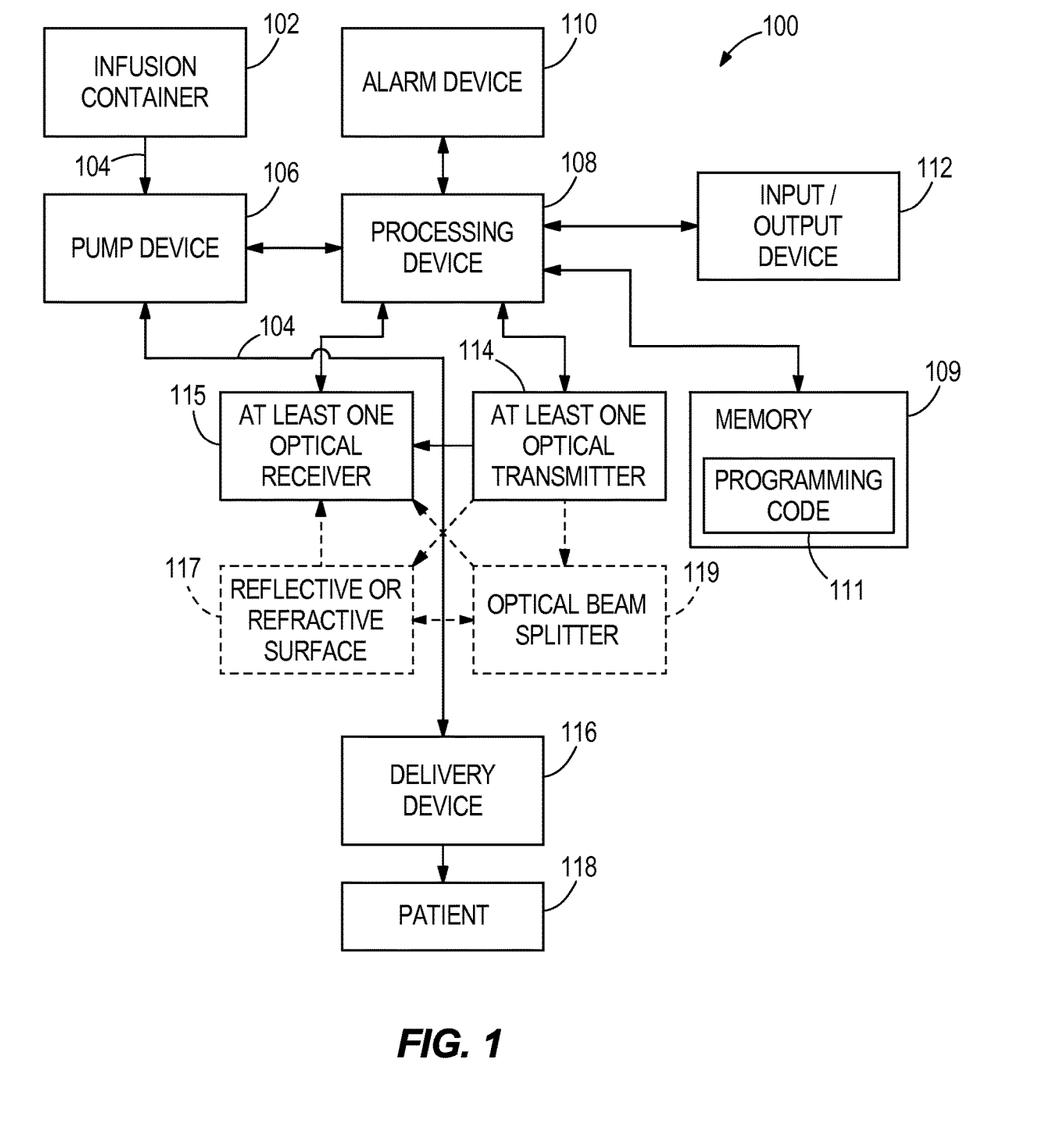
FIG. 1 illustrates a block diagram of an infusion system under one embodiment of the disclosure.

FIG. 1 illustrates a block diagram of an infusion system 100 under one embodiment of the disclosure. The infusion system 100 comprises: an infusion container 102; a fluid delivery line 104; a pump device 106; a processing device 108; a memory 109; an alarm device 110 that generates an audio, visual, or other sensory signal or the like to a user; an input/output device 112; at least one optical transmitter 114; at least one optical receiver 115; and a delivery device 116. The infusion system 100 may comprise an infusion system such as the Plum™, GemStar™, Symbig™, or other type of infusion system.

The infusion container 102 comprises a container for delivering an infusion fluid such as IV fluid or a drug to a patient 118. The fluid delivery line 104 comprises one or more tubes (and optionally in some embodiments includes a cassette), connected between the infusion container 102, the pump device 106, and the delivery device 116, for transporting infusion fluid from the infusion container 102, through the pump device 106, through the delivery device 116 to the patient 118. The fluid delivery line 104 may also be used to transport blood to the patient 118 using the delivery device 116, as a result of a pumping action of the pump device 106. The pump device 106 comprises a pump for pumping infusion fluid from the infusion container 102 or for pumping blood to the patient 118. The pump device 106 may comprise a plunger based pump, a peristaltic pump, or another type of pump. In other embodiments, the infusion system 100 may not contain a pump device and may use the force of gravity to deliver the infusion fluid.

The at least one optical transmitter 114 is disposed adjacent to the fluid delivery line 104. The at least one optical transmitter 114 is configured to transmit optical signals having different wavelengths through the fluid delivery line 104. In one embodiment, the transmitted optical signals comprise near infrared spectrum light having varying wavelengths ranging between 600 nanometers to 1,500 nanometers. In another embodiment, the transmitted optical signals comprise near infrared spectrum light having wavelengths ranging between 940 nanometers to 1,050 nanometers. In still other embodiments, the transmitted optical signals may comprise near infrared spectrum light having varying wavelengths. In one embodiment, the at least one transmitter 114 may transmit the optical signals having the different wavelengths sequentially. The at least one optical receiver 115 is disposed adjacent to the fluid deliver line 104 and is configured to receive the optical signals having the different wavelengths transmitted from the at least one optical transmitter 114.

In one embodiment, the wavelengths of the optical signals transmitted by the at least one transmitter 114 are chosen so that if air is disposed in the fluid delivery line 104 the air will have a substantially greater impact on one of the transmitted optical signals than on another of the transmitted optical signals. For purposes of this disclosure, the term "substantially" is defined as being greater than 10%. In another embodiment, the wavelengths of the transmitted optical signals are optimized for the particular type of the infusion fluid disposed in the fluid delivery line 104 to achieve maximum differentiation between the infusion fluid being disposed in the fluid delivery line 104 and air being disposed in the fluid delivery line 104. In still another embodiment, the at least one optical transmitter 114 and the at least one optical receiver 115 are modulated in order to achieve a high level of immunity from the ambient light presence of background light sources such as fluorescent light, light-emitting-diode light, etc. and to increase signal to noise ratio of the signal acquisition system.

In one embodiment, the at least one optical transmitter 114 and the at least one optical receiver 115 are disposed on opposite sides of the fluid delivery line 104. In another embodiment, the at least one optical transmitter 114 and the at least one optical receiver 115 are disposed on the same side of the fluid delivery line 104 and a reflective or refractive surface 117 may be disposed on the opposite side of the fluid delivery line 104 for reflecting or refracting the optical signals transmitted from the at least one optical transmitter 114, through the fluid delivery line 104, back to the at least one optical receiver 114. In another embodiment, at least one optical beam splitter 119 may be used to split the optical signal(s) transmitted by the at least one optical transmitter 114.

The processing device 108, which comprises at least one processor, is in electronic communication with the pump device 106, the memory 109, the at least one optical transmitter 114, the at least one optical receiver 115, the input/output device 112, and the alarm device 110. The memory 109 comprises programming code 111 for execution by the processing device 108. The programming code 111 is configured to determine whether air or the infusion fluid is disposed in the fluid delivery line 104 based on the received optical signals having the different wavelengths which are received by the at least one optical receiver 115. In one embodiment, the processing device 108 includes the memory 109 and the programming code 111. In another embodiment, the processing device 108 and the memory 109 may be separate components. The processing device 108 also contains or is in communication with a clock.

In one embodiment, the programming code 111 is configured to determine whether the air or the infusion fluid is disposed in the fluid delivery line 104 based how a ratio of the received optical signals having the different wavelengths which are received by the at least one optical receiver 115 compares to a threshold.

The alarm device 110 comprises an alarm, triggered or generated by the processing device 108, for notifying the clinician (also referred to as 'user' herein) of when the infusion system 100 contains air. The alarm device 110 may be configured to stop the pump device 106 prior to a significant amount of air being delivered through the fluid delivery line 104 and the delivery device 116 to the patient 118.

The input/output device 112 comprises a device, which allows a clinician to input or receive information. The input/output device 112 allows a clinician to input information such as: medication information regarding the infusion fluid being delivered from the infusion container 102; infusion information regarding the infusion of the infusion fluid being delivered from the infusion container 102; the selection of settings for the processing device 108 to apply in using the programming code containing the algorithm(s); or other information that is pertinent to the infusion. The input/output device 112 may allow a clinician to select and/or confirm a user-inputted medication infusion program to be applied by the processing device 108. The input/output device 112 may further output information to the clinician. In other embodiments, any of the information inputted into the input/output device 112 may be pre-installed into the programming code or the processing device 108. In another embodiment, the information may be remotely programmed into the processing device 108 from a remote computer or the input/output device 112 may be a remote and/or portable computer.

The delivery device 116 comprises a patient vascular access point device for delivering infusion fluid from the infusion container 102 to the patient 118, or for delivering blood to the patient 118. The delivery device 116 may comprise a needle, a catheter, a cannula, or another type of delivery device. In other embodiments, the infusion system 100 of FIG. 1 may be altered to vary the components, to take away one or more components, or to add one or more components.

Figures 2, 3:
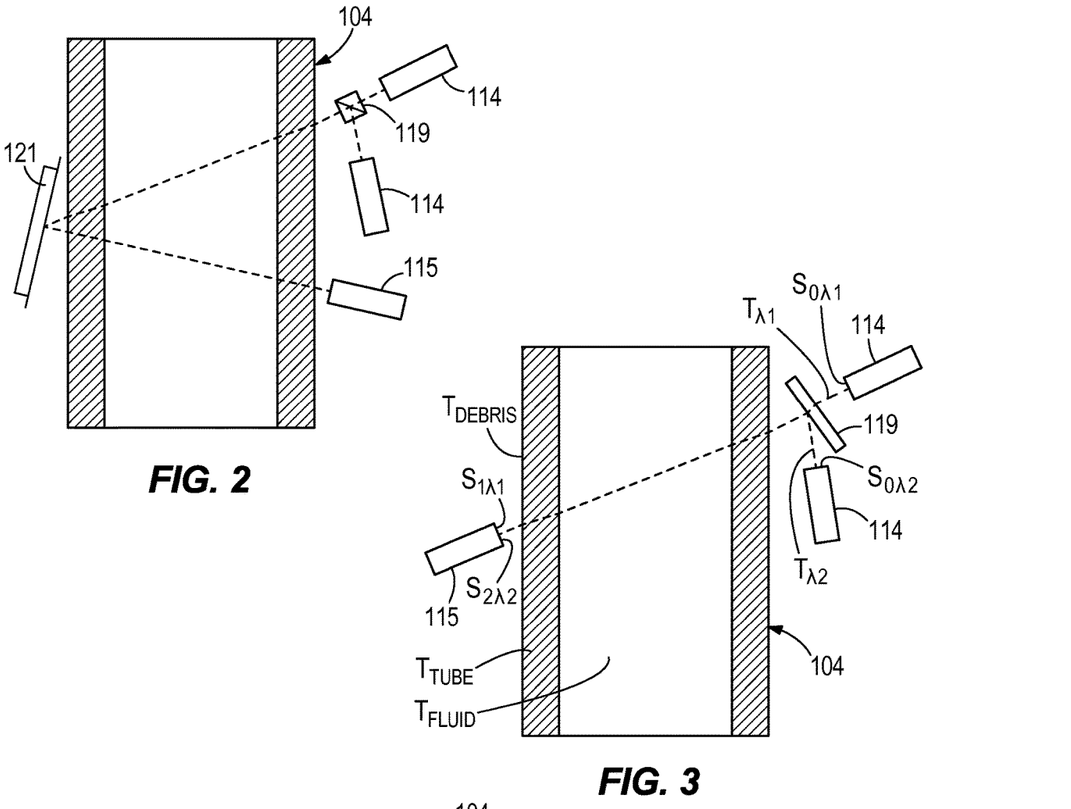
FIG. 2 illustrates a side-cross-section view of one embodiment of two optical transmitters transmitting, using alternative modulation of the transmitters, separate, sequential, alternating optical signals having different wavelengths to an optical beam splitter which directs each separate, sequential, alternating optical signal along the same optical axis through a fluid delivery line, to a mirror which reflects each separate, sequential, alternating optical signal back through the fluid delivery line to an optical receiver located on the same side of the fluid delivery line as the two optical transmitters and the optical beam splitter.
FIG. 3 illustrates a side-cross-section view of another embodiment of two optical transmitters transmitting, using alternative modulation of the transmitters, separate, sequential, alternating optical signals having different wavelengths to an optical beam splitter which directs each separate, sequential, alternating optical signal along the same optical axis through a fluid delivery line to an optical receiver located on the opposite side of the fluid delivery line as the two optical transmitters and the optical beam splitter.

FIG. 2 illustrates a side-cross-section view of one embodiment of two optical transmitters 114 transmitting optical signals having different wavelengths to an optical beam splitter 119 which directs the separate optical signals along the same optical axis through a fluid delivery line 104 to a mirror 121 which reflects the optical signals back through the fluid delivery line 104 to an optical receiver 115. In this embodiment, the transmitted optical signals of differing wavelengths may be pulsed in a sequential, alternating order. Throughout this disclosure, anytime the term mirror or optical beam splitter is used, in other embodiments any type of beam splitting device, reflective surface, or refractive surface may be substituted.

FIG. 3 illustrates a side-cross-section view of another embodiment of two optical transmitters 114 transmitting optical signals having different wavelengths to an optical beam splitter 119 which directs the transmitted optical signals along the same optical axis through the fluid delivery line 104 to an optical receiver 115. The optical receiver 115 is located on the opposite side of the fluid delivery line 104 as the two optical transmitters 114 and the optical beam splitter 119. In this embodiment, the transmitted optical signals of different wavelengths may be pulsed in a sequential, alternating order.

Figure 4:
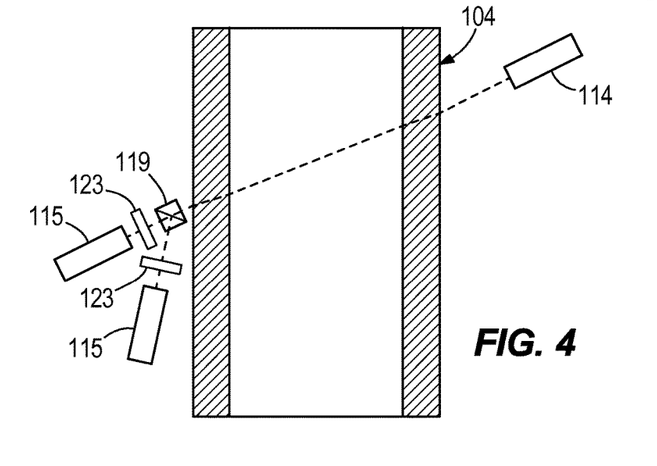
FIG. 4 illustrates a side-cross-section view of another embodiment of one optical transmitter transmitting a broad spectrum optical signal, using continuous transmission, through a fluid delivery line to a beam splitter which splits the broad spectrum optical signal into two beams that each respectively pass through separate optical filters before being received by separate optical receivers, with the optical transmitter being disposed on an opposite side of the fluid delivery line as the beam splitter, separate optical filters, and the separate optical receivers.

FIG. 4 illustrates a side-cross-section view of still another embodiment of one optical transmitter 114 transmitting continuously a broad spectrum optical signal having a spectrum of wavelengths through the fluid delivery line 104 to an optical beam splitter 119. The optical beam splitter 119 splits the optical signal into two optical beams (or two optical signals) which then each respectively pass through separate optical filters 123 before being received by separate optical receivers 115. The two optical filters 123 are configured to filter the two separate beams so that that the two separate beams have two distinctively different wavelengths with respect to each other when they reach the respective receivers 115. The optical transmitter 114 is disposed on an opposite side of the fluid delivery line 104 as the optical beam splitter 119, the optical filters 123, and the optical receivers 115.

Figure 5:
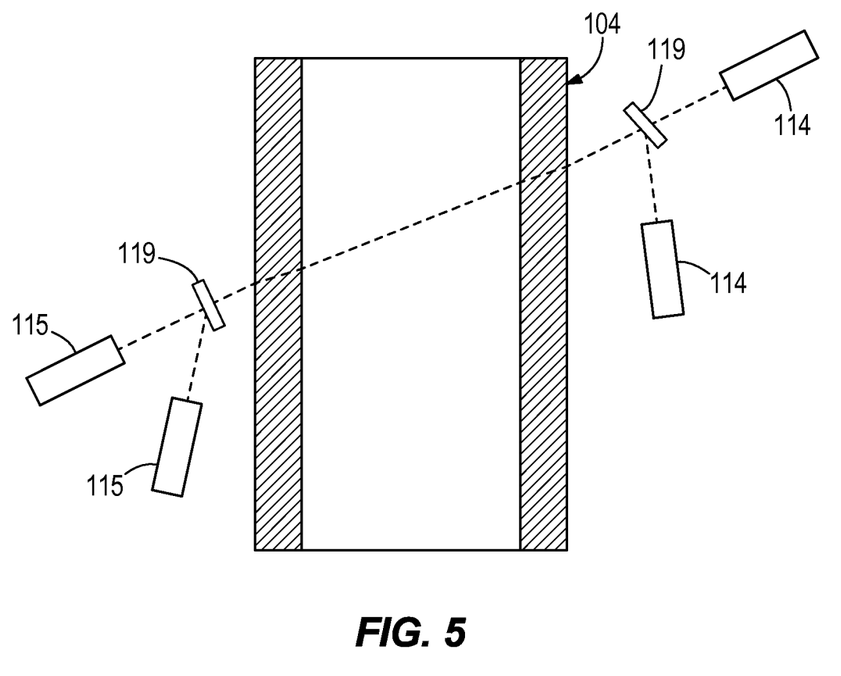
FIG. 5 illustrates a side-cross-section view of another embodiment of two optical transmitters transmitting optical signals having different wavelengths which are pulsed in a sequential, alternating order through a first beam splitter or mirror, through a fluid delivery line, to a second beam splitter or mirror which splits the optical signals into separate beams which are received by separate receivers, with the two optical transmitters, and the first beam splitter or mirror being located on an opposite side of the fluid delivery line as the second beam splitter or mirror and the separate receivers.

FIG. 5 illustrates a side-cross-section view of still another embodiment of two optical transmitters 114 transmitting optical signals having different wavelengths through a first beam splitter or mirror 119, through the fluid delivery line 104 to a second beam splitter or mirror 119 which splits the beam into two beams (i.e. two optical signals) which are received by separate optical receivers 115. The two optical transmitters 114 and the first beam splitter or mirror 119 are located on an opposite side of the fluid delivery line 104 as the second beam splitter or mirror 119 and the separate optical receivers 115. In this embodiment, the transmitted optical signals of different wavelengths may be pulsed in a sequential, alternating order.

Figure 6:
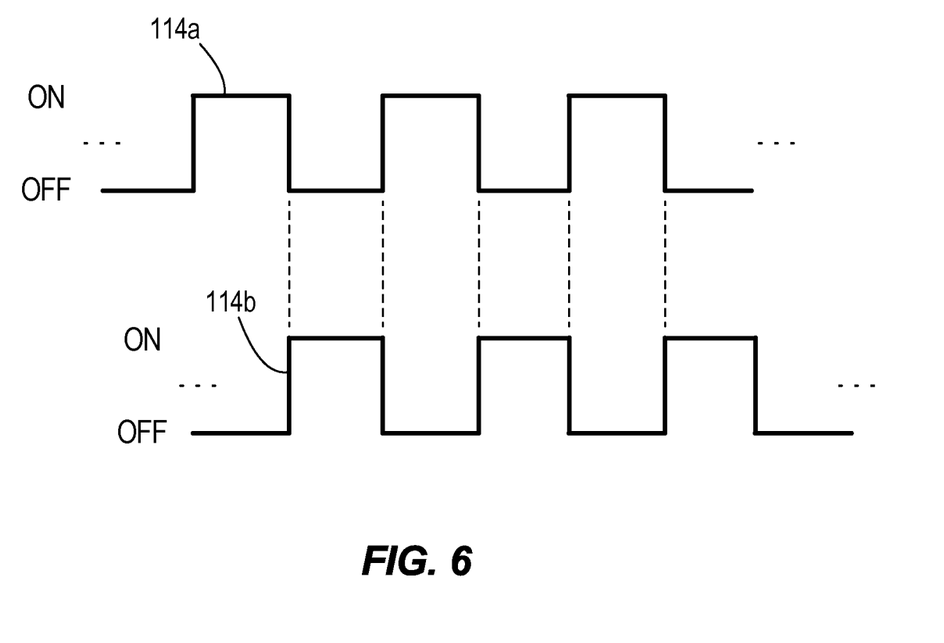
FIG. 6 illustrates graphs of one embodiment of a first optical transmitter being turned ON and OFF to transmit a first optical signal of one wavelength, and a second optical transmitter being turned ON and OFF at opposite times as the first optical transmitter to transmit a second optical signal of a different wavelength.

FIG. 6 illustrates graphs of one embodiment of a first optical transmitter 114a being turned ON and OFF to transmit a first optical signal of one wavelength, and a second optical transmitter 114b being turned on and off at opposite times as the first optical transmitter 114a to transmit a second optical signal of a different wavelength.

With reference again to FIG. 3, the optical transmission $T_{\lambda 1}$ of the first optical signal having a first wavelength transmitted by the optical transmitter 114, through the fluid delivery line 104 containing fluid, and to the optical receiver 115 is determined using the equation $T_{\lambda 1} = C$ ($T_{tube}$, $T_{fluid}$, $T_{debris}$). The equation illustrates that the optical transmission $T_{\lambda 1}$ of the first optical signal is a function of the optical transmission of the first optical signal through the fluid delivery line tubing $T_{tube}$, through the fluid $T_{fluid}$, and through the debris (i.e. dirt, residue due to cleaning solution, optical noise from ambient sources, etc.) build-up on the fluid delivery tubing $T_{debris}$. Similarly, the optical transmission $T_{\lambda 2}$ of the second optical signal having a second different wavelength transmitted by the optical transmitter 114, through the fluid delivery line 104 containing fluid, and to the optical receiver 115 is determined using the equation $T_{\lambda 2} = f$ ($T_{tube}$, $T_{fluid}$, $T_{debris}$). The equation again illustrates that the optical transmission $T_{\lambda 2}$ of the second optical signal is a function of the optical transmission of the second optical signal through the fluid delivery line tubing $T_{tube}$, through the fluid $T_{fluid}$, and through the debris build-up on the fluid delivery line tubing $T_{debris}$.

The first optical signal $S_{1\lambda 1}$ detected by the optical receiver 115 is a function of the first original signal $S_{o\lambda 1}$ having the first wavelength transmitted by the optical transmitter 114 and the optical transmission of the first original signal $S_{o\lambda1}$ through the fluid delivery line tubing $T_{tube}$, through the fluid $T_{fluid}$, and through the debris build-up on the fluid delivery line tubing $T_{debris}$ as shown by the equation $S_{1\lambda1}=S_{o\lambda1}$ f $(T_{tube}, T_{fluid}, T_{debris})$. The second optical signal $S_{2\lambda2}$ detected by the optical receiver 115 is a function of the second original signal $S_{o\lambda2}$ having the second different wavelength transmitted by the optical transmitter 114 and the optical transmission of the second original signal $S_{o\lambda2}$ through the fluid delivery line tubing $T_{tube}$, through the fluid $T_{fluid}$, and through the debris build-up on the tubing $T_{debris}$ as shown by the equation $S_{2\lambda2}=S_{o\lambda2}$ f $(T_{tube}, T_{fluid}, T_{debris})$. By taking a ratio of $S_{\lambda1/\lambda2}=S_{1\lambda1}/S_{2\lambda2}=S_{o\lambda1}$ f $(T_{tube}, T_{fluid}, T_{debris})/S_{o\lambda2}$ f $(T_{tube}, T_{fluid}, T_{debris})-S_{o\lambda1}$ f $(T_{fluid})/S_{o\lambda2}$ f $(T_{fluid})$ the portion of the signal effected by the fluid delivery line tubing and the debris transmissions cancel each other out since they remain the same during the optical signal reception process, and the resultant equation is a function of the original signals and the fluid transmission. Furthermore, the fact that the two optical transmitters are operating on the same optical axis and are modulated at a high frequency assures measurement through the same section of the moving fluid. To illustrate this, the Nyquist theorem states the sampling rate of the photo detector must be greater (at least twice) than the movement of the fluid in order to ensure that each transmitted wavelength travels through the same section of the fluid/air region. At a maximum flow rate of 1,000 milliliters per hour, the fluid moves at a speed of 133.84 millimeters per second in a typical intravenous line tubing of 1.33 millimeters inside diameter for a PVC tubing. A 0.48 millimeter fluid column in a 1.33 millimeter inside diameter tubing has a 1 microliter volume. If this fluid column moves with a speed of 133.84 millimeters per second, the 1 microliter fluid column completely leaves the region in about 0.003 seconds; thus, indicating a minimum sampling frequency of 666 Hertz (e.g. 2*Nyquist frequency of 333 Hertz). Alternatively, a sample frequency of minimum 666 Hertz is required to sample a 1 microliter fluid column in a 1.33 millimeter inside diameter IV tube. Light emitting diodes (LEDs) can be modulated in the megahertz region and can adequately sample and accommodate virtually any flow rate utilized in infusion therapies.

A simplified version of the equation when the fluid in the fluid delivery line 104 is fluid comprises $S_{\lambda1/\lambda2-fluid}=S_{1\lambda1}/S_{2\lambda2}=S_{o\lambda1}$ f $(T_{fluid})/S_{o\lambda2}$ f $(T_{fluid})=A_{fluid}$. A simplified version of the equation when air is disposed in the fluid delivery line 104 comprises $S_{\lambda1/\lambda2-air}=S_{1\lambda1}/S_{2\lambda2}=S_{o\lambda1}$ f $(T_{air})/S_{o\lambda2}$ f $(T_{air})=A_{air}$. The simplified equations illustrate that the ratios give different distinct values with $A_{fluid}$ indicating that fluid is disposed in the fluid delivery line 104 and with $A_{air}$ indicating that air is disposed in the fluid delivery line 104. As a result, these equations/ratios can be used to detect when air is in the fluid delivery line 104. The equations/ratios may give varying results for different fluids being disposed in the fluid delivery line 104 but are easily distinguishable from the results of the equations when air is disposed and present in the fluid delivery line 104.

The Beer-Lambert Law (or Beer's Law) along with the proposed ratiometric method supports the instant disclosure. The Beer's Law relates the absorption of light to the properties of the material through which the light travels. Beer's Law states that there is an exponential dependence between the transmission of the light through a substance and the product of the absorption coefficient (i.e. in this case tubing, fluid/air, dirt, residue due to cleaning solutions, etc.) of the substance and the distance the light travels through the substance (i.e. optical axis). In particular, Beer's Law states that $$T = \frac{I}{I_0} = e^{-\alpha L}$$

where T is transmission, I is intensity, $I_0$ is initial intensity, $\alpha$ is absorption coefficient, and L is the optical path length. The absorption coefficient is comprised of the absorption coefficients of the tubing, fluid/air/froth, and any residue due to the cleaning solutions or oil and dirt. More specifically, the equation can be rewritten for the intensities the optical receiver will "observe" from the two different optical wavelengths, namely $I_1=I_0 e^{-\alpha_1 L}$ and $I_2=I_0 e^{-\alpha_2 L}$, because L is a constant and as a result of the narrow separation of the different wavelengths, $a_1 \equiv a_2$. Taking the ratio of $I_1$ and $I_2$ cancels the common elements such as residue due to cleaning solution or oil and dirt, and the tubing material parameters leaving the equation to contain only the ratio of the initial intensities (which are known). Since the transmitted wavelengths share the same optical path, tubing, residue ("noise"), and sample the same section of the fluid column, the only significant difference is whether the sampled region contains air or air; thus offering immunity from noise and resulting in high signal-to-noise. A similar approach holds true for all embodiments described in this disclosure including the use of at least one transmitter and at least one receiver. The disclosure does not convey a limit on the number of transmitters or receivers which may be used in alternative embodiments.

Because this disclosure provides immunity from ambient noise (dirt, ambient light, residue from cleaning solutions, etc.) there exist the advantage of self-calibration of the optical sensor. One method of utilizing self-calibration in an infusion pump is to provide a baseline reading without the presence of the IV tubing (and cassette) and prior to loading the IV tubing (and cassette) into the infuser. Because this disclosure is not an amplitude-based optical sensor system, but rather a ratiometric method, the initial baseline reading (without the presence of the IV tubing and/or cassette) provides a reference reading. The current state of the art air sensors in the typical infusion pump is based on ultrasound technology which does not provide the opportunity to self-calibrate the ultrasound sensor nor provide immunity to mechanical changes or external noise factors (dirt, etc.). Routine calibration is typically needed for these current state of the art air sensors in infusion pumps as part of overall life-cycle management. The instant disclosure does not require calibration in the field or at the service facility as the device automatically self-calibrates before every use.

Figure 7:
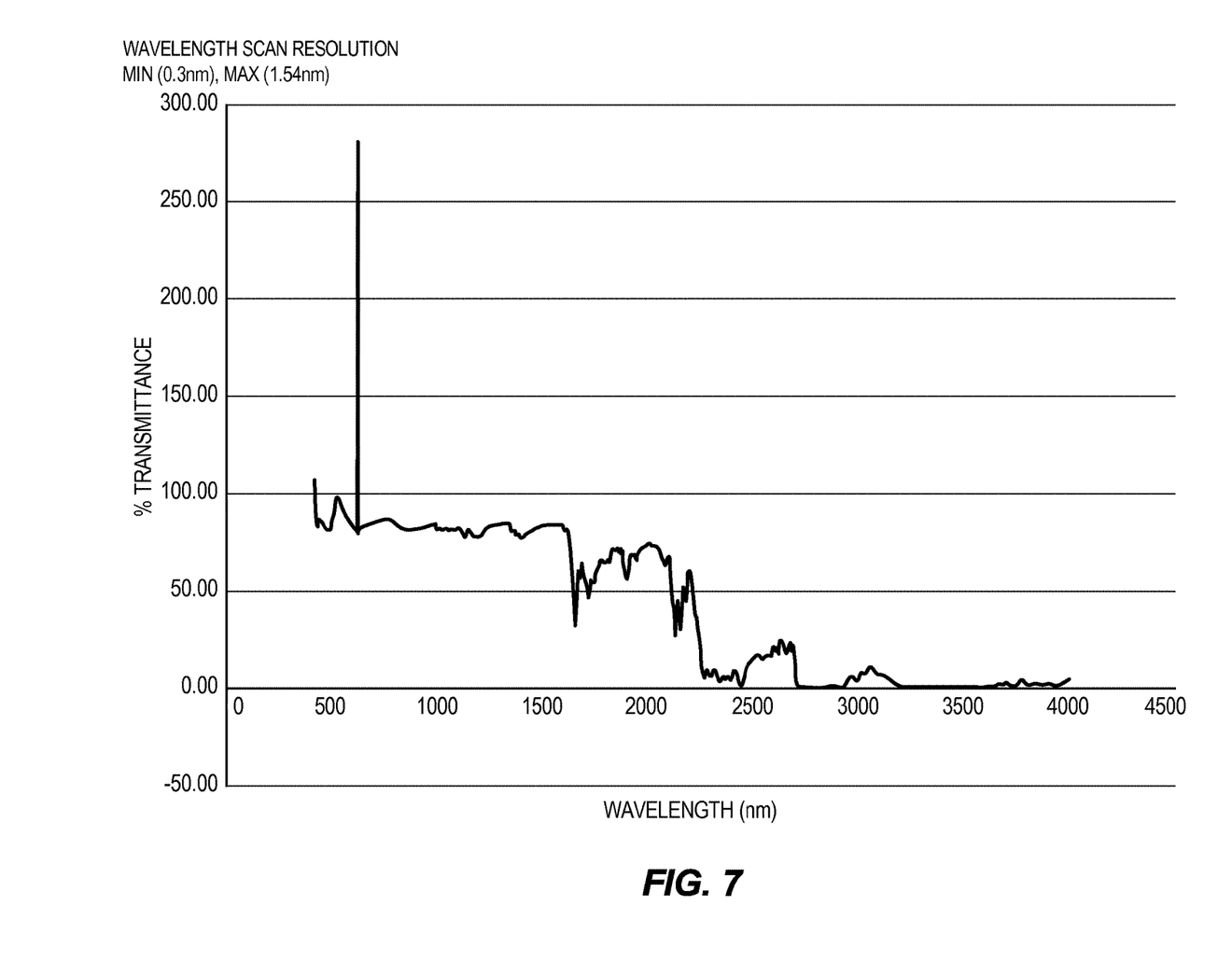
FIG. 7 is a graph illustrating spectral scan results obtained for one embodiment of a planar plastic material that was used in an infusion pump cassette.

FIG. 7 is a graph illustrating spectral scan results that were obtained for a planar plastic material that was used in an infusion pump cassette comprising part of a fluid delivery line 104. Wavelength is plotted on the X-axis and the percentage transmittance is plotted on the Y-axis. The graph shows that from about 400 nanometers to approximately 1,600 nanometers the transmittance is above 70 percent with a slight dip at around 1,600 nanometers, and returning to approximately 70 percent before indicating no transmittance as wavelength continues to increase with the scan ending at approximately 4,000 nanometers. The transmittance is greater than 70 percent in the range of 1,000 nanometers to 1,500 nanometers. FIG. 7 demonstrates that varying the wavelengths of the optical signals results in substantial changes in transmittance.

Figure 8:
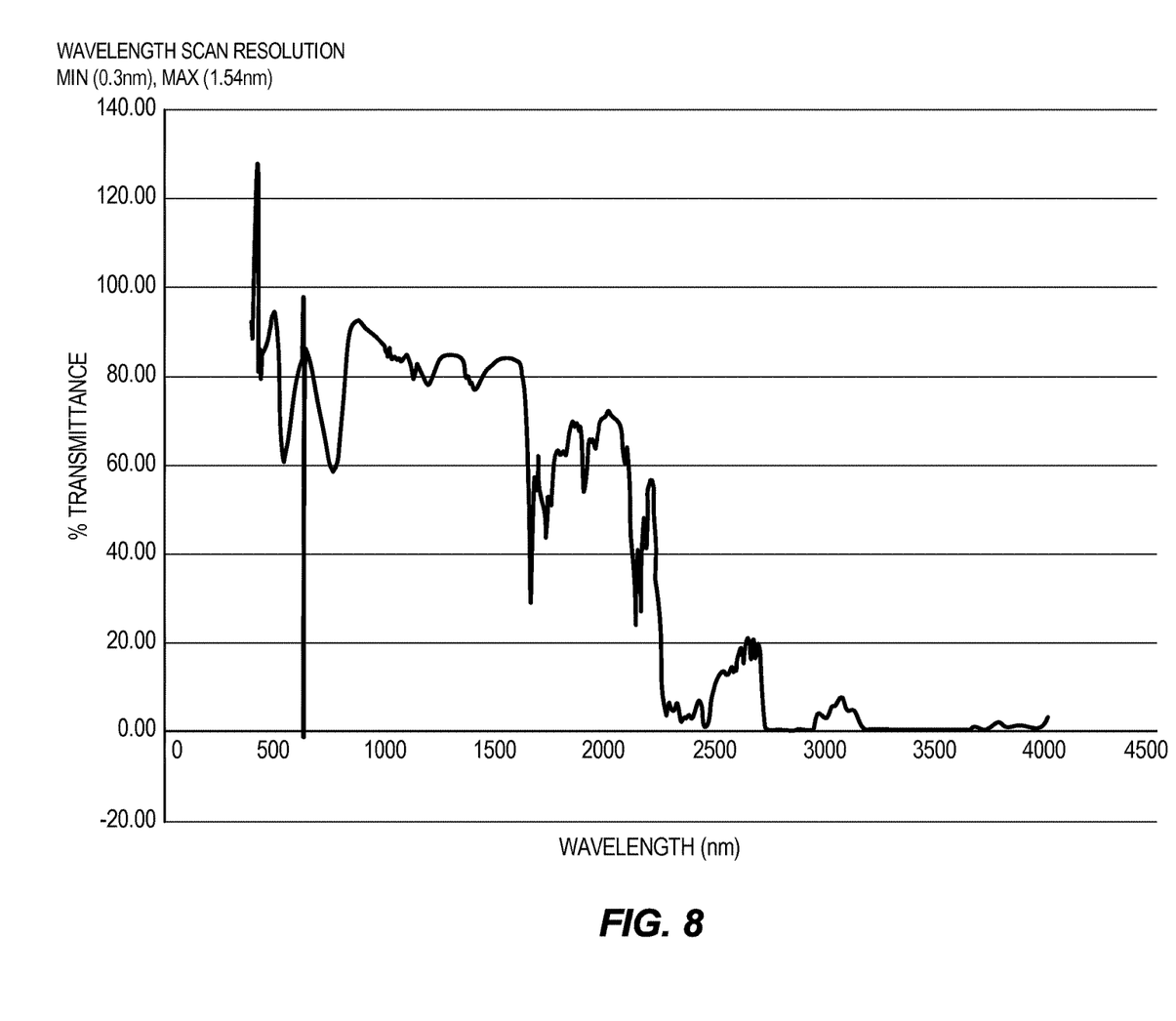
FIG. 8 is a graph illustrating spectral scan results obtained for another embodiment of the same plastic material that was used in the infusion pump cassette of FIG. 7 with the exception that the plastic material was concave.

FIG. 8 is a graph illustrating spectral scan results that were obtained for the same plastic material that was used in the infusion pump cassette of FIG. 7 with the exception that the plastic material was concave. Wavelength is plotted on the X-axis and the percentage transmittance is plotted on the Y-axis. The graph shows that the transmittance is greater than 80 percent in the range of 1,000 nanometers to 1,500 nanometers. FIG. 8 demonstrates that varying the wavelengths of the optical signals results in substantial changes in transmittance.

Figure 9:
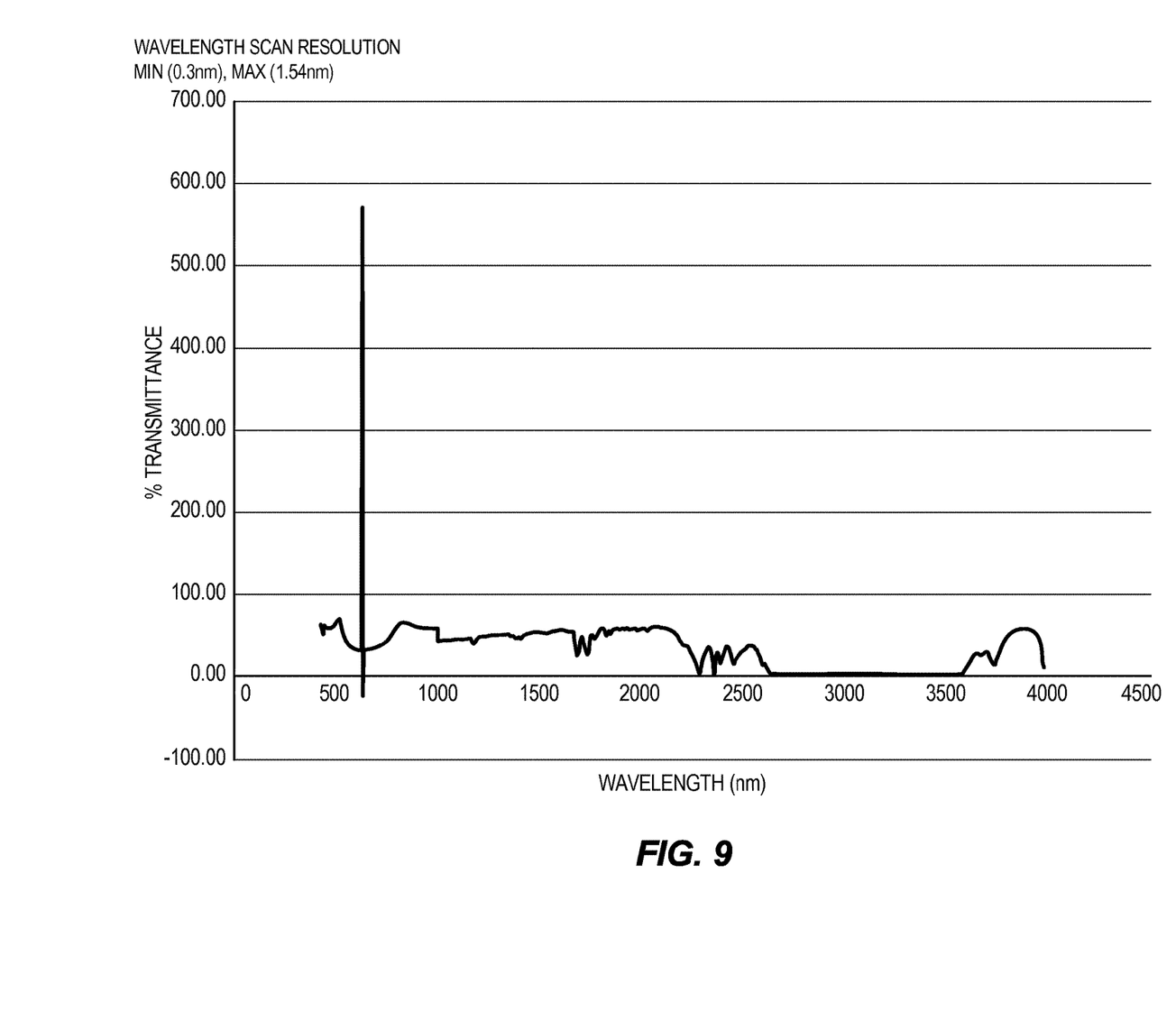
FIG. 9 is a graph illustrating spectral scan results that were obtained for yet another embodiment of a silicone membrane, which is the media containing the infusion fluid in the infusion system.

FIG. 9 is a graph illustrating spectral scan results that were obtained for a silicone membrane material that was used in an infusion pump cassette. Wavelength is plotted on the X-axis and the percentage transmittance is plotted on the Y-axis. The graph shows that the transmittance is greater than 40 percent in the range of 1,000 nanometers to 1,500 nanometers. FIG. 9 demonstrates that varying the wavelengths of the optical signals results in substantial changes in transmittance.

Figure 10:
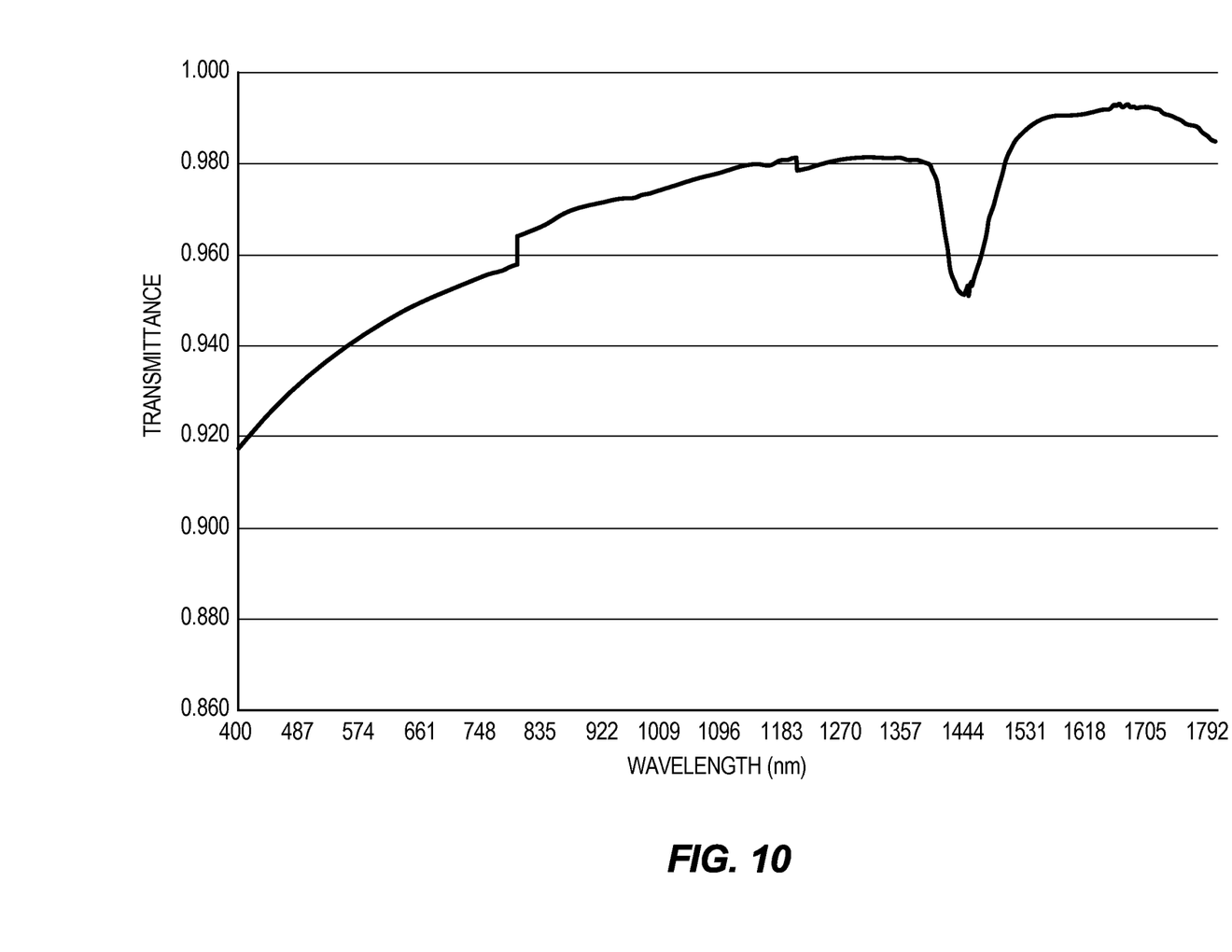
FIG. 10 is a graph illustrating spectral scan results that were obtained for another embodiment of a 0.9 percent sodium chloride solution that was delivered via a fluid delivery line of an infusion system.

FIG. 10 is a graph illustrating spectral scan results that were obtained for a 0.9 percent sodium chloride solution that was delivered via a fluid delivery line of an infusion system. Wavelength is plotted on the X-axis and the percentage transmittance is plotted on the Y-axis. The graph shows that the transmittance is greater than 90 percent in the range of 400 nanometers to 1,800 nanometers. The optical axis length was 1 mm. FIG. 10 demonstrates that varying the wavelengths of the optical signals results in substantial changes in transmittance.

Figure 11:
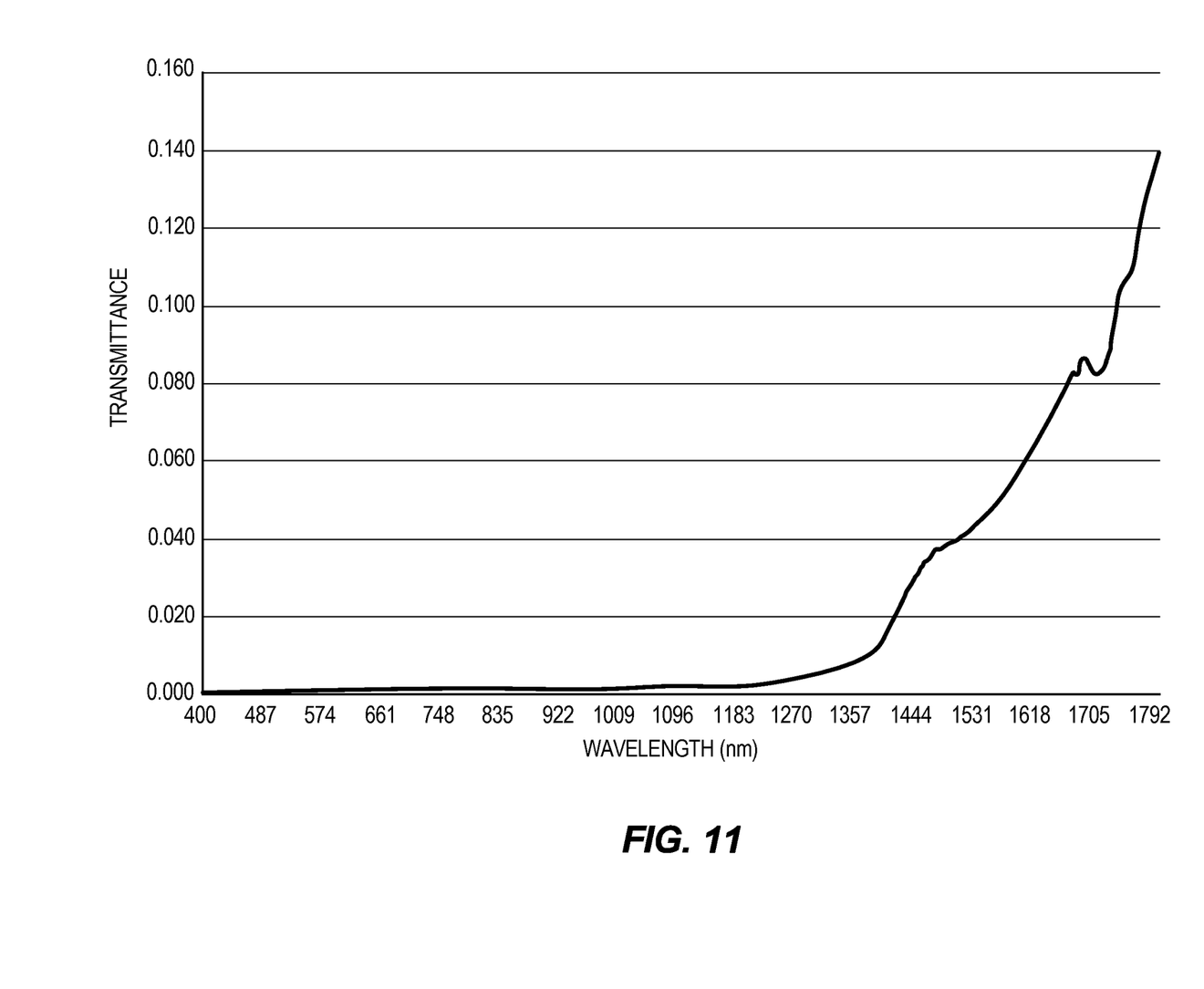
FIG. 11 is a graph illustrating spectral scan results that were obtained for yet another embodiment of an Intralipid 20 percent (fat emulsion) solution that was delivered via a fluid delivery line of an infusion system.

FIG. 11 is a graph illustrating spectral scan results that were obtained for an Intralipid 20 percent (fat emulsion) solution used in a fluid delivery line of an infusion system. Wavelength is plotted on the X-axis and the percentage transmittance is plotted on the Y-axis. The graph shows that the transmittance is minimal in the range of 400 nanometers to approximately 1,200 nanometers and then increases with wavelength until the end of the scan at approximately 1,800 nanometers. The optical axis length was 1 nanometers. FIG. 11 demonstrates that varying the wavelengths of the optical signals results in substantial changes in transmittance.

Figure 12:
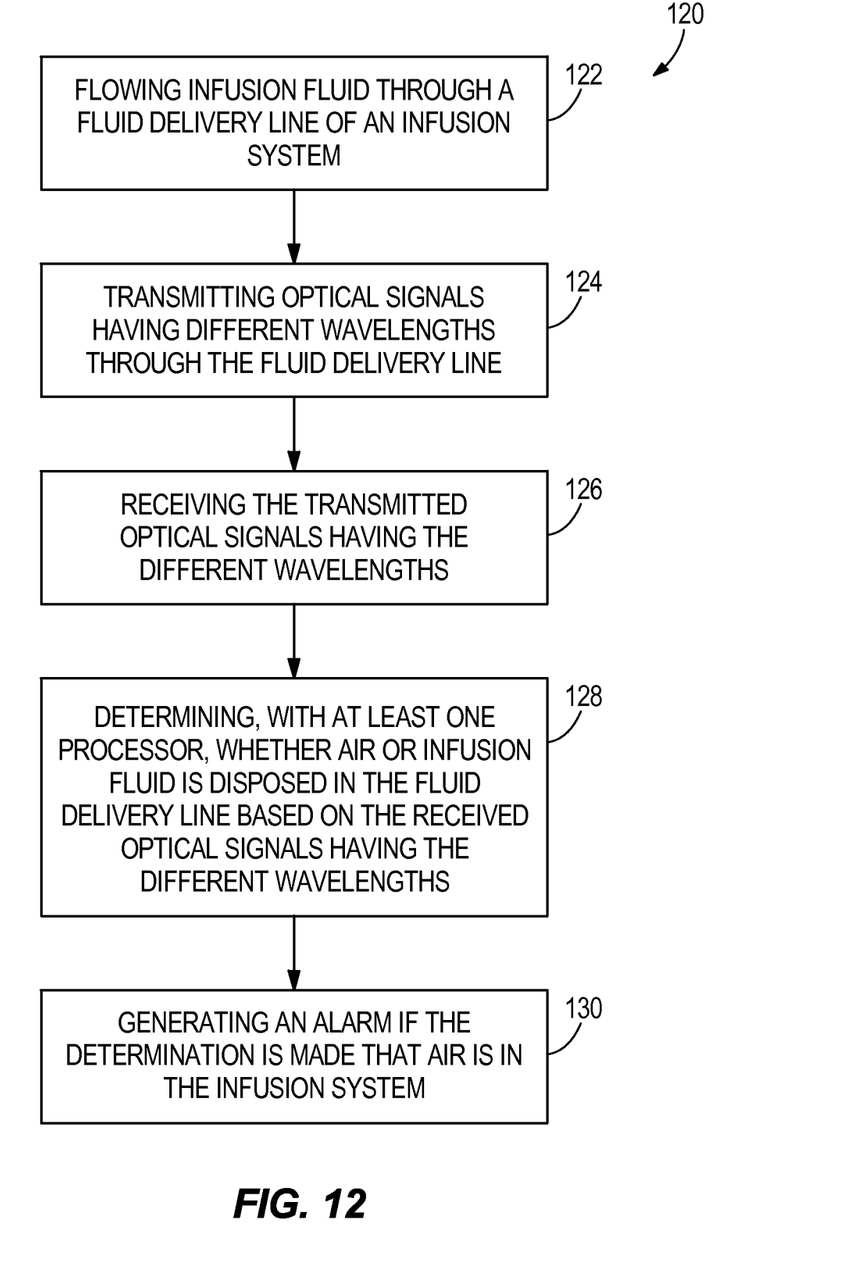
FIG. 12 illustrates a flowchart for one method of signal acquisition according to one embodiment of the disclosure.

FIG. 12 illustrates a flowchart of one embodiment of a method 120 for infusing an infusion fluid. The method 120 may utilize the infusion system 100 of FIG. 1. In other embodiments, the method 120 may utilize varying systems including but not limited to any system disclosed herein. In step 122, the infusion fluid is flowed through a fluid delivery line of an infusion system. In step 124, optical signals are transmitted having different wavelengths through the fluid delivery line. In one embodiment, the different wavelengths of the optical signals were optimized for the particular type of infusion fluid disposed in the fluid delivery line to achieve maximum differentiation between the infusion fluid being disposed in the fluid delivery line and air being disposed in the fluid delivery line.

In one embodiment, the optical signals comprise near infrared spectrum light having varying wavelengths ranging between 600 nanometers and 1,500 nanometers. In another embodiment, the transmitted optical signals comprise near infrared spectrum light having varying wavelengths ranging between 940 nanometers and 1,050 nanometers. In other embodiments, the transmitted optical signals may comprise light having varying wavelengths. In another embodiment, the at least one optical transmitter transmitting the optical signals may be modulated in order to achieve a high level of immunity from the ambient light presence of background light sources such as fluorescent light, light-emitting-diode light, etc. and to increase signal to noise ratio of the signal acquisition system. In step 126, the transmitted optical signals having the different wavelengths are received.

In step 128, at least one processor determines whether air or infusion fluid is disposed in the fluid delivery line based on the received optical signals having the different wavelengths. In one embodiment, step 128 comprises the at least one processor determining whether the air or the infusion fluid is disposed in the fluid delivery line based on how a ratio of the received optical signals having the different wavelengths compares to a threshold. In one embodiment, step 128 comprises the at least one processor determining the transmittance property of the infusion fluid or air in-between two spectral regions. In step 130, if the determination is made in step 128 that air is in the infusion system an alarm is generated by the at least one processor 108 and the alarm device 110 generates the appropriate sound or visual display to notify the user. In one embodiment, step 130 may comprise the at least one processor turning off a pump of the infusion system if the alarm sounds.

In one embodiment, steps 124, 126, and 128 comprise: in step 124, transmitting a first optical signal having a first wavelength and transmitting a second optical signal having a second wavelength different than the first wavelength through the fluid delivery line; in step 126, receiving the first optical signal and the second optical signal; and in step 128, determining with the at least one processor whether air or infusion fluid is disposed in the fluid delivery line based on the received optical signals having the different wavelengths with the at least one processor finding that air disposed in the fluid delivery line has a substantially greater impact on the received first optical signal than on the second received optical signal.

In one embodiment, steps 124 and 126 comprise: in step 124, two optical transmitters transmitting the optical signals having the different wavelengths through the fluid delivery line; and in step 126, only one optical receiver receiving the transmitted optical signals having the different wavelengths.

In one embodiment, steps 124 and 126 comprise: in step 124, two optical transmitters transmitting the optical signals having the different wavelengths through the fluid delivery line; and in step 126, two optical receivers receiving the transmitted optical signals having the different wavelengths.

In one embodiment, steps 124 and 126 may utilize at least one optical transmitter and at least one optical receiver disposed on opposite sides of the fluid delivery line. In another embodiment, steps 124 and 126 may utilize at least one optical transmitter and at least one optical receiver disposed on the same side of the fluid delivery line, and a reflective or refractive surface disposed on the opposite side of the fluid delivery line for reflecting or refracting the optical signals transmitted from the at least one optical transmitter, through the fluid delivery line, back to the at least one optical receiver.

In other embodiments, any number, configuration, orientation, or location of optical transmitters and optical receivers may be used. In still other embodiments, an optical beam splitter may be used to direct the optical signals to travel along a common optical axis. In further embodiments, a reflective or refractive surface may be used to reflect or refract the optical signals having the different wavelengths to the at least one optical receiver. In other embodiments, additional components may be used in combination with at least one optical transmitter and at least one optical receiver to assist in transmitting or receiving the optical signals. In other embodiments, the method 120 may be altered to vary the order or substance of any of the steps, to delete one or more steps, or to add one or more steps.

Applicant has conducted testing using various infusion fluids (including Sodium Chloride 0.9 percent; Dextrose 50 percent; Intralipid 20 percent; and Egg White 4.7 percent) and various flow rates (including 250 milliliters per hour; 500 milliliters per hour; and 1,000 milliliters per hour) to compare the results of using the optical system and method of the disclosure to determine whether air is disposed in the fluid delivery line of an infusion system versus using an ultrasound sensor system (piezoelectric crystal transmitter receiver pair interfaced with electronic voltage sweep oscillator that sweeps through the sensor's peak coupling frequency) to make this determination. The testing has revealed that the optical system and method of the disclosure has substantial unexpected results over use of the ultrasound sensor. Use of the optical system and method of the disclosure resulted in an improvement in resolution, defined as the smallest bubble size the sensor can detect, for all of the tested infusion fluids at each of the various flow rates of up to 72 percent improvement over use of the ultrasound sensor. Use of the optical system and method of the disclosure resulted in an improvement in accuracy, defined as the rate of detection, for all of the tested infusion fluids at each of the various flow rates in a range of 6 to 72 percent improvement over use of the ultrasound sensor. Use of the optical system and method of the disclosure resulted in an improvement in signal-to-noise calculation for all of the tested infusion fluids at each of the various flow rates in a range of 280 to 800 percent improvement over use of the ultrasound sensor. Use of the optical system and method of the disclosure resulted in an improvement in dynamic range, defined as the difference between the largest and smallest bubble the sensor was able to detect, for all of the tested infusion fluids at each of the various flow rates of up to 10.7 percent improvement over use of the ultrasound sensor.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. Furthermore, it is to be understood that the disclosure is defined by the appended claims. Accordingly, the disclosure is not to be restricted except in light of the appended claims and their equivalents.

What is claimed is:

1. A method of determining whether air is disposed in infusion fluid in a fluid delivery line of an infusion system:
   transmitting a first optical signal at a first wavelength through the fluid delivery line;
   transmitting a second optical signal at a second wavelength that is different than the first wavelength through the fluid delivery line;
   directing the transmitted first optical signal and the transmitted second optical signal along a same optical axis through the fluid delivery line; and
   receiving the first and second optical signals after propagation through the fluid delivery line;
   determining a ratio corresponding to the received first optical signal and the received second optical signal along the optical axis; and
   determining whether air is disposed in the infusion fluid in the fluid delivery line based on the ratio corresponding to the received first and second optical signals.

2. The method of claim 1, wherein the same optical axis lies inside the fluid delivery line.

3. The method of claim 1, wherein the directing is performed by a beam splitter.

4. The method of claim 1, wherein the ratio enables self calibration.

5. The method of claim 1, wherein the first wavelength is selected such that when air is disposed in the fluid delivery line, the air will have a substantially greater impact on the first optical signal than on the second optical signal.

6. The method of claim 1, wherein the first wavelength and the second wavelength are selected based on a particular type of the infusion fluid disposed in the fluid delivery line to achieve maximum differentiation between the air disposed in the fluid delivery line and the infusion fluid disposed in the fluid delivery line.

7. A method for determining whether air is disposed in infusion fluid in a fluid delivery line of an infusion system, the method comprising:
   receiving a first optical signal of a first wavelength propagating through the fluid delivery line;
   receiving a second optical signal of a second wavelength that is different than the first wavelength propagating through the fluid delivery line, wherein the first optical signal and the second optical signal are directed along a same optical axis through the fluid delivery line;
   determining a ratio corresponding to the received first optical signal and the received second optical signal along the optical axis; and
   determining whether air is disposed in the infusion fluid in the fluid delivery line based on the ratio.

8. The system of claim 7, wherein the same optical axis lies inside the fluid delivery line.

9. The method of claim 7, wherein the directing is performed by a beam splitter.

10. The method of claim 7, wherein the ratio enables self calibration.

11. The method of claim 7, wherein the first wavelength is selected such that when air is disposed in the fluid delivery line, the air will have a substantially greater impact on the first optical signal than on the second optical signal.

12. The method of claim 7, wherein the first wavelength and the second wavelength are selected based on a particular type of the infusion fluid disposed in the fluid delivery line to achieve maximum differentiation between the air disposed in the fluid delivery line and the infusion fluid disposed in the fluid delivery line.

13. A system for determining whether air is disposed in infusion fluid in a fluid delivery line of an infusion system, the system comprising one or more hardware processors configured to:

receive a first optical signal of a first wavelength propagating through the fluid delivery line;

receive a second optical signal of a second wavelength that is different than the first wavelength propagating through the fluid delivery line, wherein the first optical signal and the second optical signal are directed along a same optical axis through the fluid delivery line;

determining a ratio corresponding to the received first optical signal and the received second optical signal along the optical axis; and determine whether air is disposed in the infusion fluid in the fluid delivery line based on the ratio corresponding to the received first and second optical signals.

14. The system of claim 13, wherein the same optical axis lies inside the fluid delivery line.

15. The system of claim 13, wherein the directing is performed by a beam splitter.

16. The system of claim 13, wherein the ratio enables self calibration.

17. The system of claim 13, wherein the first wavelength is selected such that when air is disposed in the fluid delivery line, the air will have a substantially greater impact on the first optical signal than on the second optical signal.

* * * * *